United States Patent
Puchhammer

(10) Patent No.: US 8,579,991 B2
(45) Date of Patent: Nov. 12, 2013

(54) HAND PROSTHESIS AND FORCE TRANSMISSION DEVICE

(75) Inventor: Gregor Puchhammer, Vienna (AT)

(73) Assignee: Otto Bock Healthcare GmbH, Duderstadt (DE)

( * ) Notice: Subject to any disclaimer, the term of this patent is extended or adjusted under 35 U.S.C. 154(b) by 235 days.

(21) Appl. No.: 12/097,800

(22) PCT Filed: Dec. 7, 2006

(86) PCT No.: PCT/DE2006/002175
§ 371 (c)(1),
(2), (4) Date: Jun. 17, 2008

(87) PCT Pub. No.: WO2007/076763
PCT Pub. Date: Jul. 12, 2007

(65) Prior Publication Data
US 2008/0319553 A1    Dec. 25, 2008

(30) Foreign Application Priority Data
Dec. 20, 2005  (DE) .......................... 10 2005 061 266

(51) Int. Cl.
*A61F 2/54*   (2006.01)
(52) U.S. Cl.
USPC .............................................. 623/64; 623/24
(58) Field of Classification Search
USPC ................ 623/57, 63–65; 901/30, 32, 36, 38
See application file for complete search history.

(56) References Cited

U.S. PATENT DOCUMENTS

| | | | |
|---|---|---|---|
| 908,881 A | | 1/1909 | Nelson |
| 1,225,415 A | | 5/1917 | Cronemiller |
| 1,347,004 A | * | 7/1920 | Beck ............................... 623/63 |
| 1,630,277 A | | 5/1927 | Smith |
| 2,433,301 A | | 12/1947 | Simpson |
| 2,464,577 A | * | 3/1949 | Hobbs ............................. 623/63 |
| 2,549,716 A | * | 4/1951 | Simpson ......................... 623/64 |
| 2,553,827 A | | 5/1951 | Mason |
| 2,847,678 A | * | 8/1958 | Opuszenski .................... 623/64 |
| 2,859,450 A | | 11/1958 | Becker |
| 3,026,534 A | | 3/1962 | Brown |
| 4,114,464 A | | 9/1978 | Schubert et al. |
| 4,149,278 A | | 4/1979 | Frosch et al. |
| 4,246,661 A | | 1/1981 | Pinson |

(Continued)

FOREIGN PATENT DOCUMENTS

| | | |
|---|---|---|
| DE | 19854762 | 6/2000 |
| DE | 19906294 | 9/2000 |

(Continued)

OTHER PUBLICATIONS

International Search Report for PCT/DE2006/002175, 3 pgs., mailed Aug. 3, 2007.

(Continued)

*Primary Examiner* — David Isabella
*Assistant Examiner* — Marcia Hoffman
(74) *Attorney, Agent, or Firm* — Holland & Hart LLP

(57) ABSTRACT

A hand prosthesis includes a chassis to which at least one finger prosthesis is articulated. The finger prosthesis is swivelable about at least one swiveling axis by a drive that is connected to the finger prosthesis via a force transmission device. The force transmission device does not yield to tension and is flexible.

6 Claims, 6 Drawing Sheets

(56) References Cited

U.S. PATENT DOCUMENTS

| | | | |
|---|---|---|---|
| 4,315,650 A | 2/1982 | Yoshida | |
| 4,364,593 A * | 12/1982 | Maeda | 294/106 |
| 4,623,354 A | 11/1986 | Childress et al. | |
| 4,643,473 A | 2/1987 | Douglas | |
| 4,685,924 A | 8/1987 | Massey | |
| 4,685,929 A | 8/1987 | Monestier | |
| 4,921,293 A | 5/1990 | Ruoff et al. | |
| 4,955,918 A | 9/1990 | Lee | |
| 5,080,682 A | 1/1992 | Schectman | |
| 5,888,246 A | 3/1999 | Gow | |
| 6,660,043 B2 | 12/2003 | Kajitani et al. | |
| 6,896,704 B1 * | 5/2005 | Higuchi et al. | 623/64 |
| 8,118,805 B2 * | 2/2012 | Jinno et al. | 606/1 |
| 2003/0195638 A1 | 10/2003 | Kajitani et al. | |
| 2004/0015240 A1 | 1/2004 | Archer et al. | |
| 2005/0021154 A1 | 1/2005 | Brimalm | |

FOREIGN PATENT DOCUMENTS

| | | |
|---|---|---|
| DE | 20301116 | 3/2003 |
| DE | 10237373 | 3/2004 |
| EP | 0045818 | 2/1982 |
| EP | 0219478 | 10/1986 |
| EP | 1195151 | 4/2002 |
| FR | 2236478 | 2/1975 |
| GB | 1201182 | 8/1967 |
| GB | 1175830 | 12/1969 |
| GB | 1585256 | 6/1976 |
| GB | 1571140 | 11/1977 |
| WO | WO 03/017876 | 3/2003 |
| WO | WO 03/017880 | 3/2003 |

OTHER PUBLICATIONS

International Search Report and Written Opinion issued in PCT/DE2006/002177, 9 pages, mailed Aug. 3, 2007.

International Search Report and Written Opinion issued in PCT/DE2006/002176, 9 pages, mailed Aug. 3, 2007.

Non-Final Office Action mailed Aug. 28, 2009 for U.S. Appl. No. 12/097,804, 19 pages.

Non-Final Office Action mailed Aug. 24, 2009 for U.S. Appl. No. 12/097,798, 14 pages.

* cited by examiner

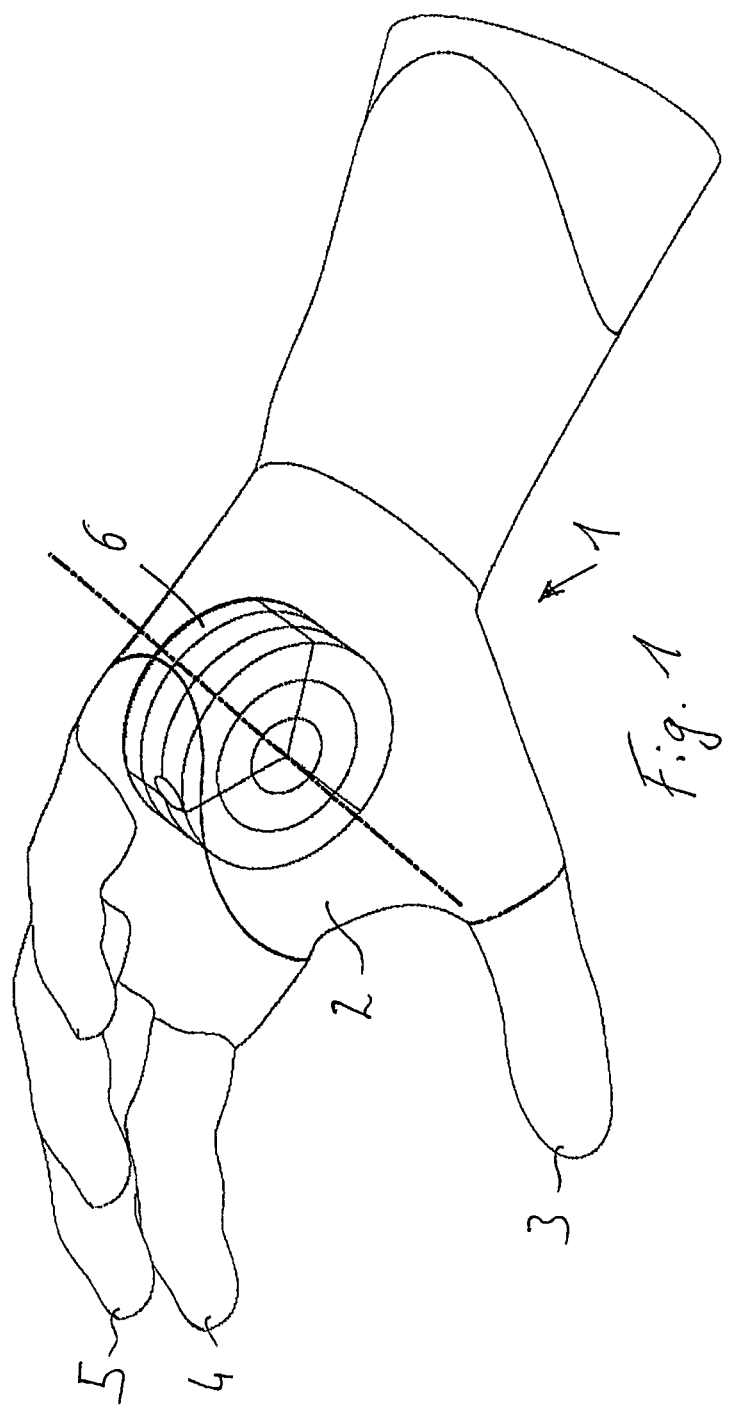

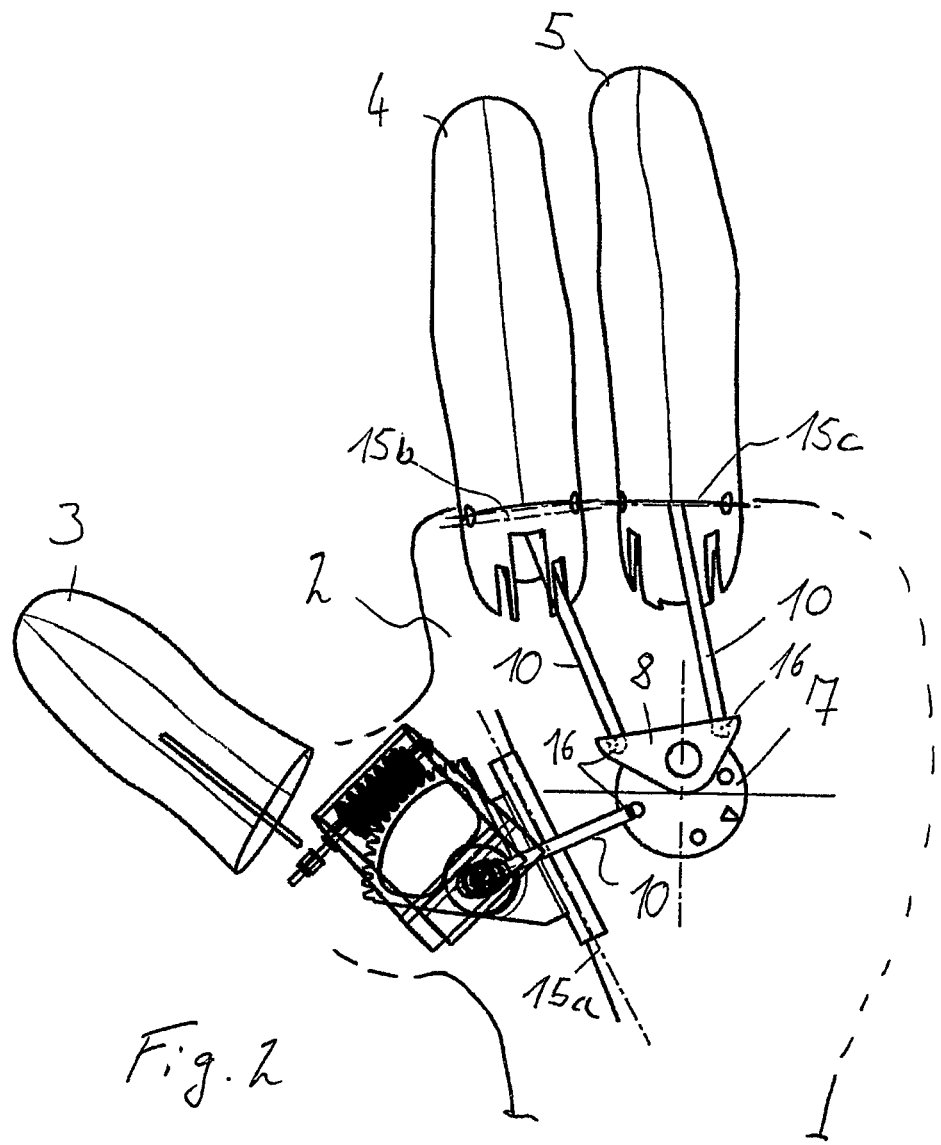

ously without the force transmission unit undergoing any elongation. For this purpose, the force transmission unit may have a component comprising a cable, stranded wire or fiber, via which the tensile forces are transmitted. This cable, stranded-wire or fiber component may be produced from a wire cable or high-strength fibers such as carbon fibers, aramid or glass fibers, natural fibers other synthetic fibers. The cable, stranded-wire or fiber component may be formed as a closed loop, open loop or a twisted loop. The connection of the two open ends of the cable or stranded wire or the fastening in the remaining material or to the drive or the finger prosthesis may take place by twisting, splicing or adhesive bonding. Whenever a cable component is mentioned hereafter, fiber or stranded-wire components are also included.

HAND PROSTHESIS AND FORCE TRANSMISSION DEVICE

CROSS-REFERENCE TO RELATED APPLICATIONS

This application is a national stage application, filed pursuant to 35 U.S.C. §371, of PCT/DE2006/00002175 filed Dec. 7, 2006, which claims priority to DE 10 2005 061 266.0 filed Dec. 20, 2005, which are herein incorporated by reference in their entirety.

TECHNICAL FIELD

The invention relates to a hand prosthesis comprising a chassis, to which at least one finger prosthesis is articulated, said finger prosthesis being movable about at least one swiveling axis by means of a drive which is connected to the finger prosthesis by means of a force transmission unit.

If a hand has to be amputated or has been irreversibly severed from an arm by an accident, the appearance and some of the function of the hand can be replaced by a hand prosthesis. For this purpose, the hand prosthesis must be capable of displacing gripping devices, which may be formed as replicas of fingers, in relation to one another, in order to allow gripping of an object.

Apart from a two-finger gripper, as is known from US 2004/0015240 A1, hand prostheses which have a drive that is rigidly connected to a hand chassis by means of a bevel gear mechanism are proposed. Depending on the direction of rotation of the drive, the finger prostheses are thereby moved toward or away from one another. This drive may be activated by means of myoelectrical signals. Such a hand prosthesis is described in US 2005/0021154 A1. The appearance of such a hand prosthesis looks less natural.

An object of the present invention is to provide a hand prosthesis and a force transmission unit, resulting in a design and function that resembles the natural appearance of a hand.

In one embodiment, the hand prosthesis according to the invention comprises a chassis to which at least one finger prosthesis is articulated. The finger prosthesis is movable about at least one swiveling axis by means of a drive which is connected to the finger prosthesis by means of a force transmission unit. The force transmission unit between the drive and the finger prosthesis is yielding under pressure or elastic under bending and rigid under tension. Conventional hand prostheses provide a rigid coupling between the drive and the finger prosthesis. However, the pressure-yielding or elastic coupling of the drive to the finger prosthesis according to the present invention allows the finger prosthesis to give way under pressure loading of the force transmission unit, which is the effect of a force that brings about closing of the hand or reduction of the angle between the finger prosthesis and the hand chassis.

Apart from a natural looking appearance, this also has the effect of minimizing the stress on the mechanical components. The stress on the components is minimized because the sometimes considerable forces that occur if the finger prostheses happen to knock against an object is not transmitted directly via the force transmission unit to the drive. Rather, the flexurally elastic, preferably resilient, configuration of the force transmission unit allows displacement and conversion of the forces acting on the finger prosthesis into a movement. This movement may take place up to the maximum bending angle of the finger prosthesis.

Another embodiment of the present invention allows an unhindered and reliable, as well as precise, closing movement of the finger prosthesis, starting from an open basic position. The force transmission unit is formed so as to be rigid under tension such that tensile forces are transmitted as far as pos- In one embodiment, the force transmission unit has an elastomer component, by which it is possible to set the flexure or elasticity of the force transmission unit over a wide range. A suitable choice of an elastomer material, at least partially encloses or completely takes up the cable component. This produces a body that is dimensionally stable in the position of rest, on the one hand has very high tensile forces on account of the incorporated cable component and has desired elastic characteristics under bending and pressure.

In one embodiment, the force transmission unit may be configured as a spring-damper unit, in particular as a pneumatic unit, in which the volume of air is compressed under pressure loading, expands once the force of the pressure is no longer applied and brings about a return displacement of a pneumatic piston, and consequently of the finger prosthesis. Alternatively, the force transmission unit may be formed as a spring, which may be pre-stressed.

For coupling the force transmission unit to the drive and the finger prosthesis, bearing bushes are provided, embedded in the force transmission unit. These bearing bushes are enclosed by the elastomer element or the elastomer component, and are located within the cable or fiber component, for example, within the cable or fiber loop.

To provide a return movement of a finger prosthesis bent in the direction of the inner surface of the hand chassis, the force transmission unit is formed in a resiliently elastic manner. When not being subjected to a tensile force, the finger prosthesis is moved back into a starting position by the drive or by a transmission element coupled to the drive. This starting position corresponds to a slightly opened hand. The force transmission unit is consequently capable of transmitting a limited compressive force. A corresponding articulation or formation of the force transmission unit allows slight overextension of the finger prostheses, starting from the basic position. The spring rate of the force transmission unit is, in this case, set to return the finger prothesis into the starting position when the force transmission unit is subjected to the force of a pressure, that is to say, when the finger prosthesis swivels in the direction of the inner surface of the hand chassis. The returning force must therefore be so great that the retaining and frictional forces within the hand prosthesis.

In one embodiment, a number of force transmission units are mounted at a common bearing point and the bearing point is displaceable in relation to the swiveling axes of the finger prostheses in order to bring about bending of the finger prostheses. The common bearing point may be arranged directly on the drive or on a driven element of a gear mechanism. The common mounting facilitates synchronicity of the bending movements.

In another embodiment, two force transmission units may be connected to each other by means of a common cable, fiber or stranded-wire component, the common cable, fiber or stranded-wire component, which may be mounted at the common bearing point and on different finger prostheses. The cable, fiber or stranded-wire component transmits the tensile force that is produced by the drive via the common bearing point. This is due to the displacement in relation to the swiveling axes of the finger prostheses to the finger prostheses and brings about bending of the finger prostheses. In this case, the cable, fiber or stranded-wire component can slide along on the bearing point and in this way facilitates uniform bending of the connected finger prostheses.

The force transmission units may be fastened to a rocker, which is mounted at the common bearing point. The force transmission units may be fastened to the rocker at different distances from the common bearing point, to allow the respective finger prostheses to be adapted to the geometrical conditions within the hand prosthesis or to the conditions of use.

The force transmission unit may be formed so as to be flexibly elastic in a number of orientations, so that under compressive loading in the direction of the longitudinal axis, the bearing points are displaceable in relation to one another. The omnidirectionally flexing force transmission unit acts like a ball joint and compensates for deviations from the ideal axial position. In such embodiments, it may be possible to dispense with rotatable mounting about the axes.

The force transmission unit for the allows easy and inexpensive coupling of the drive and the finger prosthesis as well as effective transmission of tensile forces. In addition, the force transmission unit provides mounting that yields to unwanted loading and easy return.

BRIEF DESCRIPTION OF THE DRAWINGS

An exemplary embodiment of the invention is explained in more detail below on the basis of the accompanying figures. The same designations denote the same elements in the different figures, in which:

FIG. 1 shows a schematic representation of a hand prosthesis;

FIG. 2 shows a schematic partial representation of the functional setup of a hand prosthesis;

DETAILED DESCRIPTION

Figure 3A:
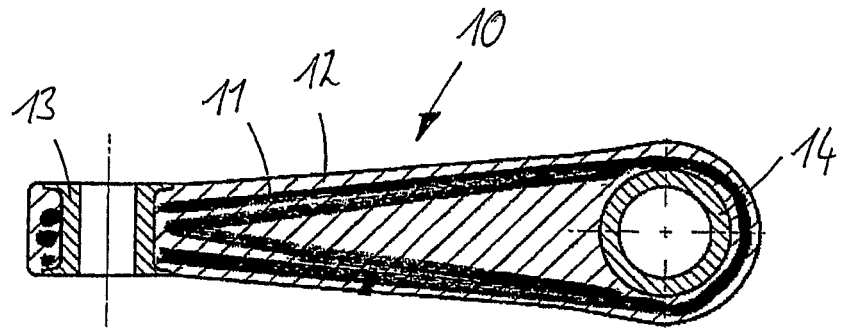
FIGS. 3a-3d show a force transmission unit in different views.

FIG. 1 shows a hand prosthesis 1, comprising a hand chassis 2 and at least three finger prostheses 3, 4, 5 articulated to the hand chassis 2. The finger prostheses 3, 4, 5 correspond to the thumb, index finger and middle finger respectively, of a natural hand. Movable mounting of these three finger prostheses 3, 4, 5 which can be actuated by means of a drive 6 is adequate to allow a plurality of gripping tasks of a hand to be performed. The two other fingers, the ring finger and the small finger, can be passively moved along with the other fingers and consist of an elastomer material, to achieve an appearance that looks as natural as possible. The drive 6 is mounted within the hand chassis 2 in the form of an electric motor with an associated gear mechanism (as shown in other figures). A power source for the drive 6 (not shown or represented), may likewise be located within the hand chassis 2. The drive 6 is activated by means of a control device (also not shown), which may likewise be located in the hand chassis 2. The corresponding signals may be generated by means of a remote control or take the form of myoelectrical signals.

FIG. 2 shows a schematic representation of the functional mode of the hand prosthesis 1. The three finger prostheses 3, 4, 5 are mounted on the hand chassis 2 such that they can swivel about articulating axes 15a-c. The finger prostheses 3, 4, 5 are connected via force transmission units 10, (the construction of which is described in detail further below, to a rotary disk 7, which is driven by the electric motor 6. The force transmission units 10 are mounted on the rotary disk 7 on spindles 16, either directly or by way of a rocker 8, which is rotatably mounted on the rotary disk 7. The rotary disk 7 itself is mounted either directly on an output shaft of the drive 6 or on an output shaft of a gear-mechanism mounted to the drive 6.

If the drive 6 is activated, the rotary disk 7 is moved by a corresponding rotational angle. As a result, the spindles 16 are displaced in relation to the swiveling axes 15a-c of the finger prostheses 3, 4, 5, which leads to a swiveling of the finger prostheses 3, 4, 5. This is due to the tensionally rigid formation of the force transmission units 10 and an articulation of the force transmission units 10 on the finger prostheses 3, 4, 5 that is at a distance from the axes of rotation 15a-c. If the drive 6 is reversed and the rotary disk 7 moves into a position in which the spindles 16 are at a minimal distance from the swiveling axes 15a-c of the finger prostheses 3, 4, 5, the opened starting position of the rotary disk 7 and drive 6 is reached. The finger prostheses 3, 4, 5 then move into their opened starting position, as a result of the resiliently elastic properties of the force transmission units 10. It is provided here that the force transmission units 10 can transmit much higher tensile forces than compressive forces. This corresponds to the physiological conditions of a natural hand, which can apply much greater forces when closing the hand than when opening it. For reasons of overall clarity, the ring finger and the small finger are not represented; they can be passively articulated to the middle finger 5 and thereby moved along with it.

FIG. 3a shows a force transmission unit 10 in a sectional representation. This unit comprises a cable or fiber component 11, which in the present case is formed as a loop. The cable component 11 may comprise a number of standard wires or individual loops, take the form of a steel cable or plastic cable or consists of some other high-strength fiber material. The cable component 11 is embedded in an elastomer element or component 12, whereby the force transmission unit 10 is given a dimensionally stable, but flexibly elastic form. The elastomer component 12 may consist of a silicone, a rubber or some other elastic material. In spite of the dimensional stability, a deformation, in particular bending, caused by compressive forces acting on the force transmission unit 10 is possible. The deformation is a result of the flexibility of the cable or fiber component 11 and the elastic characteristics under pressure or bending of the elastomer component 12. This allows the finger prostheses 3, 4, 5 that are coupled to the drive 6 or the rotary disk 7 via the force transmission unit 10 to be displaced in the direction of the inner surface of the hand chassis 2 by the compressive forces. A return displacement-takes place as a result of the resiliently elastic characteristics of the force transmission units 10, when the corresponding counteracting compressive force is no longer applied.

Located within the loop of the cable or fiber component 11 are two bearing bushes 13, 14, which are likewise embedded in the elastomer component 12. The bearing bushes 13, 14 are mounted on corresponding spindles on the finger prostheses 3, 4, 5 and on spindles 16 on the rotary disk 7 or the bridge 8. The bearing bushes 13, 14 are made of, for example of bronze, in order to form a sliding mounting with the corresponding spindles 16. For reasons of overall clarity, the coupling spindles on the finger prostheses 3, 4, 5 are not represented. These coupling spindles lie at a distance from the axes of rotation 15a-c. Thus, a torque is produced about the axes of rotation 15a-c by applying tensile forces via the force transmission units 10, which leads to a corresponding displacement of the finger prostheses 3, 4, 5.

Figure 3B:
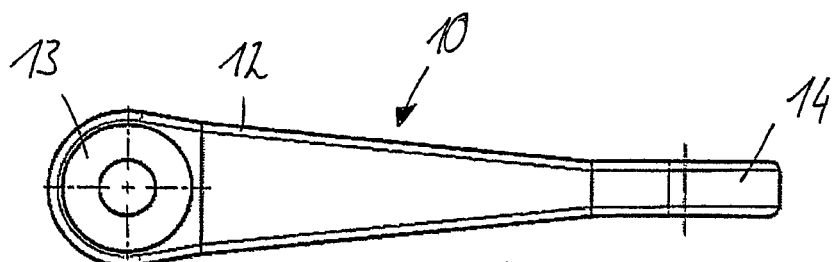
Figure 3C:
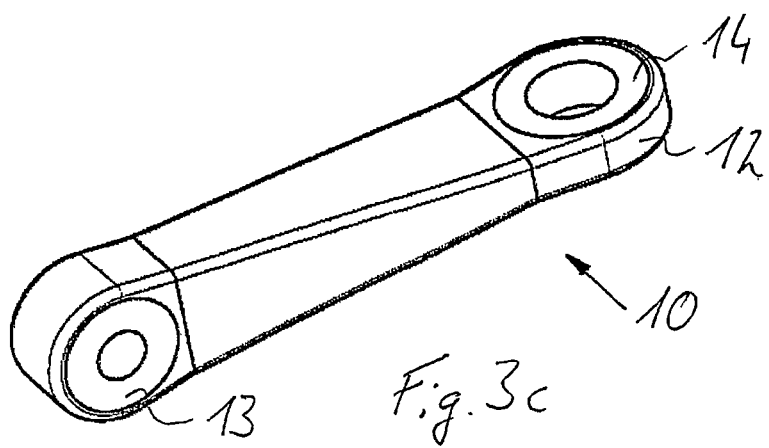

In FIGS. 3b and 3c it can be seen that the axes of rotation of the bearing bushes 13, 14 are perpendicular in relation to each other. The reason for this is due to the actual arrangement of the rotary disk 7 and the spindles 16 arranged on it or assigned to it. The axes of rotation of the bearing bushes 13, 14 may also be aligned parallel or at some other angle in relation to each other.

Figure 3D:
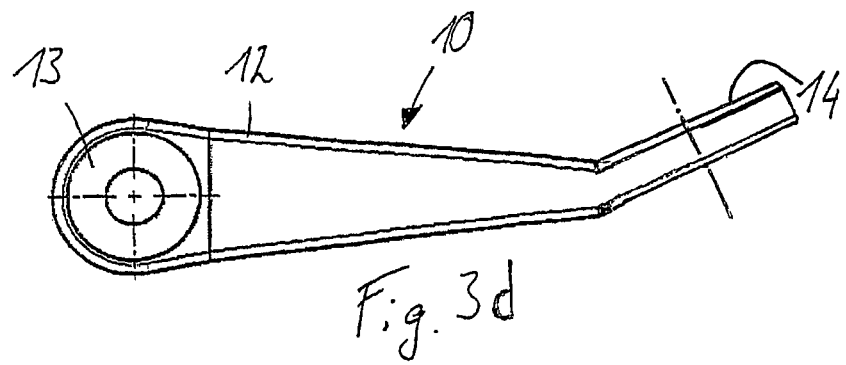

It can likewise be seen in FIGS. 3a to 3c that the cable or fiber component 11 is completely embedded in the elastomer 12. On the one hand, the cable or fiber component 11 is thereby protected from external influences and, on the other hand, the dimensional stability of the force transmission unit 10 is increased. FIG. 3d shows a deformed shape of the force transmission unit 10, which has been subjected to compressive loading in the longitudinal direction and buckled. The bearing bush 14 is no longer at right angles to the bearing bush 13, as represented in FIGS. 3a to 3c, but instead the deformation brings about a skewed position of the bearing bushes 13, 14 in relation to each other, and consequently of the axes of rotation 15, 16. On account of the elastic deformability, the force transmission unit 10 acts in a number of orientations as a ball joint and can also compensate for skewed axial positions, caused for example by production tolerances.

In another embodiment, the force transmission unit 10 may also be produced from some other element or material that yields under pressure. One example is a resiliently elastic and tensionally rigid element, such as a resilient buckling or deflecting rod or a correspondingly designed wire loop.

The compressively elastic mounting described above keeps impact forces from being directly transmitted via the finger prostheses 3, 4, 5 to the drive 6 or the rotary disk 7. Rather, unintentional knocking movements are absorbed and damped. Apart from enhancing a natural looking appearance of the hand prosthesis 1, this also increases the service life of the mountings and drive components, for example in the event of a fall.

In another embodiment the spring-damper force transmission unit 10 may also be equipped with a corresponding control, for example by means of a pneumatic or hydraulic cylinder with corresponding valve control. The unit 10 can thus effectively transmit tensile forces but provides the ability to yield elastically under compressive forces. A pneumatic configuration has the effect of bringing about a return displacement of the inwardly bent finger prostheses.

Given an adequately flexibly elastic configuration of the cable component 11, the elastomer component 12 may be omitted. Given adequate tensile strength of the elastomer component 12, it may be formed as the only force transmission unit 10.

Figure 4:
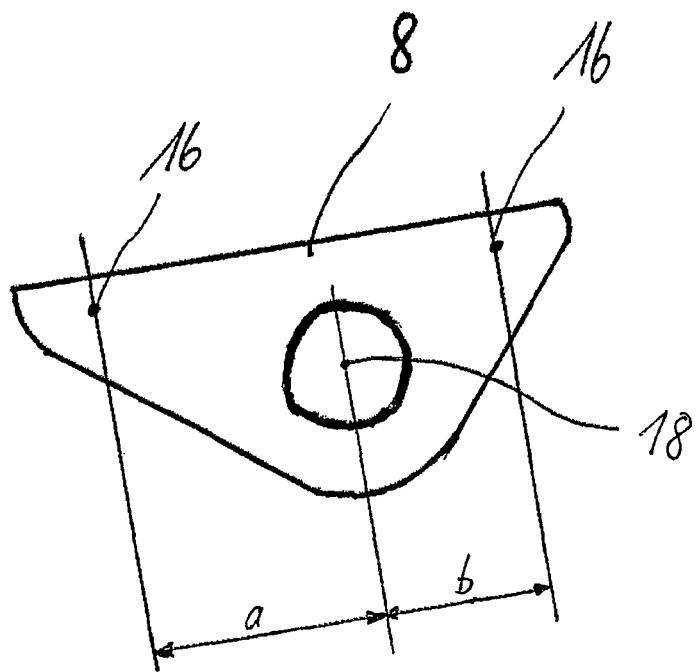
FIG. 4 shows a detailed representation of a rocker.

FIG. 4 shows the rocker 8 in an enlarged representation on its own. The rocker 8 has a common bearing point 18 in the form of a bush, which can be fitted onto a corresponding spindle on the rotary disk 7 (not shown or represented). The rocker 8 may be mounted on this spindle rotatably about the common bearing point 18, and has fastening points at the rotating spindles 16 for force transmission units 10 (not shown or represented). The distances a, b of the rotating spindles 16 or fastening points from the center of rotation of the common bearing point 18 may differ to make it possible to allow for the geometrical or mechanical conditions within the hand prosthesis 1.

Figure 5:
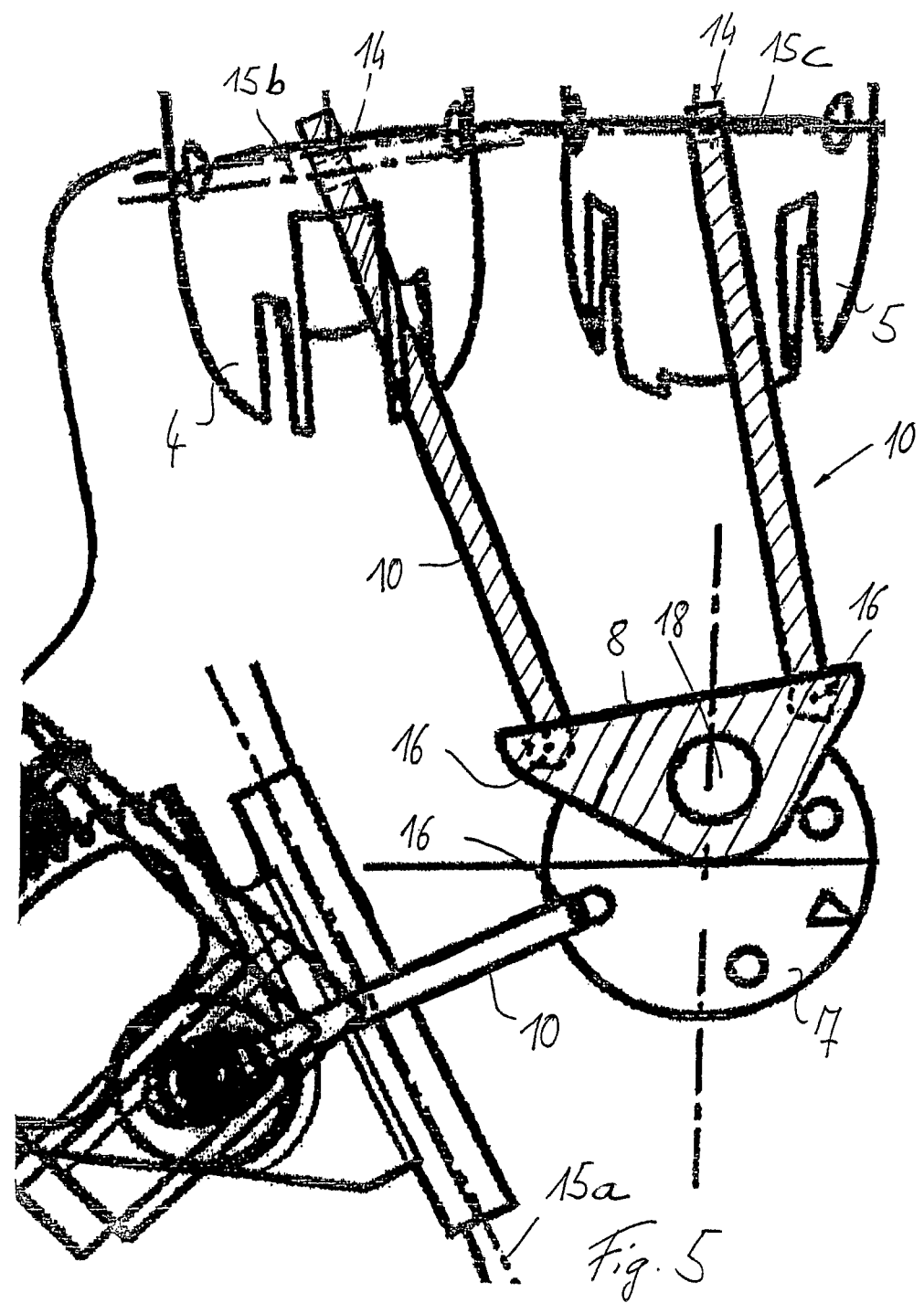
FIG. 5 shows a detailed representation from FIG. 2.

FIG. 5 is a detail view from FIG. 2 on an enlarged scale. Two force transmission units 10, which are separately formed, are mounted at the common bearing point 18 by means of the rocker 8. Alternatively, the force transmission units 10 may also be mounted on the rotary disk 7 without rocker 8, at a common bearing point or a common axis. The bearing bushes 14 assigned to the finger prostheses 4, 5 are substantially at right angles to the rotating spindles 16 on the rocker 8, but may also be skewed thereto, as indicated by the index finger 4.

Figure 6:
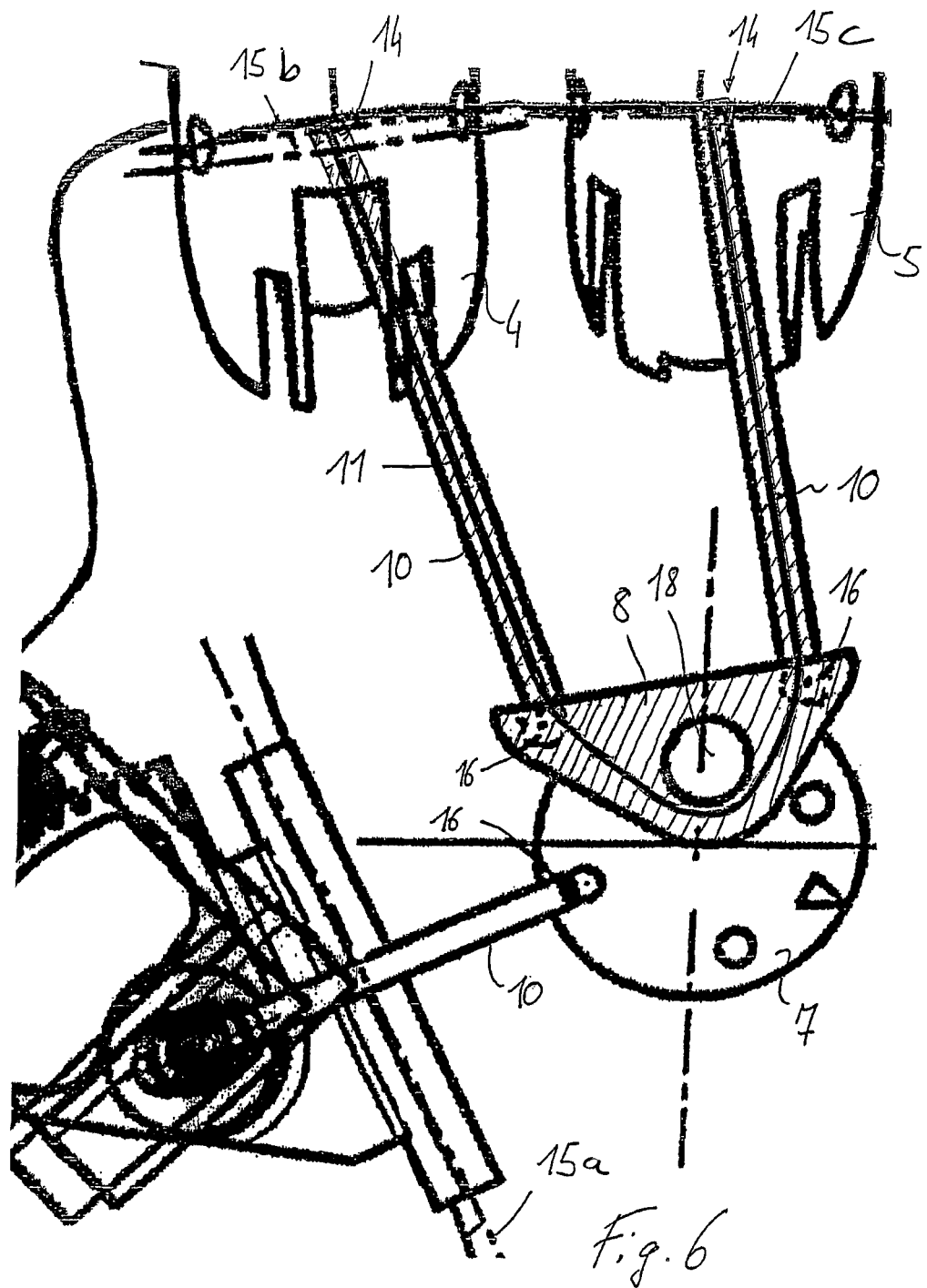
FIG. 6 is a variant of FIG. 5.

FIG. 6 is a variation of the configuration of FIG. 5, in which the cable component 11 is formed as an open loop which is fastened to the bearing bushes 14, for example by welding or adhesive attachment. The cable component 11 connects the two bearing bushes 14 of the index-finger and middle-finger prostheses 4, 5, it is partially embedded in the elastomer component of the force transmission units 10. In the region of the rocker 8, the cable component 11 is led behind the common bearing point 18 or around the axis of rotation on the rotary disk 7 and absorbs the tensile forces caused by the displacement of the common bearing point 18 in relation to the axes of rotation 15. These tensile forces are transmitted to the bearing bushes 14 through the cable component 11 and, on account of the bearing bushes 14 being mounted at a distance from the axes of rotation 15, a torque about the axes of rotation 15 is created, to bend finger prostheses 4, 5.

The invention claimed is:

1. A hand prosthesis comprising:
   a chassis;
   at least two finger prostheses mounted to the chassis about at least one swiveling axis;
   a drive mounted to the chassis;
   at least two force transmission units each being coupled between one of the at least two finger prostheses and a common bearing point, the at least two force transmission units being rigid under tension and yielding under pressure, and the common bearing point being displaceable relative to the at least one swiveling axis;
   a common cable, fiber or stranded-wire component extending between the force transmission units and wrapping around the common bearing point;
   wherein displacing the common bearing point relative to the at least one swiveling axis with the drive pivots the at least two finger prostheses about the at least one swiveling axis.

2. The hand prosthesis as claimed in claim 1, wherein the at least two force transmission units each comprise an elastomer component.

3. The hand prosthesis as claimed in claim 2, wherein the elastomer components at least partially enclose the cable, fiber or stranded-wire component.

4. The hand prosthesis as claimed in claim 1, wherein at least two force transmission units are fastened to a rocker mounted at the common bearing point.

5. The hand prosthesis as claimed in claim 4, wherein the at least two force transmission units fasten the rocker at different distances from the common bearing point.

6. The hand prosthesis claimed as in claim 1, wherein the at least two force transmission units comprise bearing bushes having axes of rotation, and the axes of rotation of the bearing bushes of each force transmission unit are arranged perpendicular relative to each other.

* * * * *